(12) United States Patent
Schiffman

(10) Patent No.: US 8,536,190 B2
(45) Date of Patent: Sep. 17, 2013

(54) TREATING UNWANTED OCULAR CONDITIONS USING AN ASCOMYCIN MACROLACTAM

(75) Inventor: Rhett M. Schiffman, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 1053 days.

(21) Appl. No.: 12/014,938

(22) Filed: Jan. 16, 2008

(65) Prior Publication Data

US 2009/0180986 A1 Jul. 16, 2009

Related U.S. Application Data

(60) Provisional application No. 60/887,177, filed on Jan. 30, 2007.

(51) Int. Cl.
*A61K 31/44* (2006.01)

(52) U.S. Cl.
USPC .......................................... 514/279; 514/912

(58) Field of Classification Search
USPC ................................. 514/279, 912
See application file for complete search history.

(56) References Cited

U.S. PATENT DOCUMENTS

| | | | |
|---|---|---|---|
| 6,667,337 B2 * | 12/2003 | Wilson | 514/449 |
| 6,699,493 B2 | 3/2004 | Wong | |
| 6,726,918 B1 | 4/2004 | Wong et al. | |
| 7,202,209 B2 | 4/2007 | Chang et al. | |
| 7,276,476 B2 | 10/2007 | Chang et al. | |
| 7,288,520 B2 | 10/2007 | Chang et al. | |
| 2002/0187998 A1 * | 12/2002 | Ueno | 514/291 |
| 2004/0054374 A1 | 3/2004 | Weber et al. | |
| 2004/0087612 A1 * | 5/2004 | English et al. | 514/291 |
| 2004/0137059 A1 | 7/2004 | Nivaggioli et al. | |
| 2005/0025810 A1 * | 2/2005 | Peyman | 424/427 |
| 2007/0015692 A1 | 1/2007 | Chang et al. | |
| 2007/0015694 A1 | 1/2007 | Chang et al. | |
| 2007/0015710 A1 | 1/2007 | Chang et al. | |
| 2007/0149447 A1 | 6/2007 | Chang et al. | |

OTHER PUBLICATIONS

Banker et al., "Modern Pharmaceutics", 1996, Marcel Decker, 3rd Edition, 596.*
Wolff, Manfred E., Berger's Medicinal Chemistry, 1995, John Wiley &Sons, Inc., 5th Ed. Part 1, 975-977.*
Testa, Prodrug research; futilie or fertile?, 2004, Biochemical Pharmacology, 68, 2097-2106.*
Testa et al., Predicting drug metabolism: Concepts and challenges, 2004, Pure Appl.Chem, vol. 76, No. 5, 907-914.*
Selim et al., Eye Cancer Therapy Tocicity Issues-5-FU (5-Fluorouracil), Aug. 2002, printed from http://www.cancersupportivecare.com/eye.html with Google date sheet of entry to the internet,3 pages.*
www.virtualmedicalcentre.com, Taxotere, Jun. 2003, printed from http://www.virtualmedicalcentre.com/drugs.asp?drugid=1713 &title=Taxotere with Google date sheet of entry to the internet, 4 pages.*
Selim et al., Eye Cancer Therapy Tocicity Issues-5-FU (5-Fluorouracil), Aug. 12, 2002, printed from http://web.archive.org/web/20020812123233/http://www.cancersupportivecare.com/eye.html, 2 pages.*
Kanski, Jack J. And Bowling, Brad "Lacrimal Drainage System, Chapter 2" in: *Clinical Ophthalmology a Systematic Approach*, 7th edition, (Elsevier Limited, 2011), pp. 65-78.
U.S. Appl. No. 11/181,187, filed Jul. 13, 2005.
U.S. Appl. No. 11/181,428, filed Jul. 13, 2005.
U.S. Appl. No. 11/255,821, filed Oct. 19, 2005.
U.S. Appl. No. 11/679,934, filed Feb. 28, 2007.
Reynolds et al, "Calcineurin inhibitors and sirolimus: mechanisms of action and applications in dermatology", Clinical and Experimental Dermatology, 2002, 27, 555-561.
Smith, "New approaches to topical therapy", Clinical and Experimental Dermatology, 2000, 25, 567-574.
U.S. Appl. No. 11/181,409, filed Jul. 13, 2005, Chang et al.
U.S. Appl. No. 11/181,509, filed Jul. 13, 2005, Chang et al.
U.S. Appl. No. 11/181,178, filed Jul. 13, 2005, Chang et al.
U.S. Appl. No. 11/161,218, filed Jul. 27, 2005, Tien et al.
U.S. Appl. No. 60/727,684, filed Oct. 17, 2005, Tien et al.

* cited by examiner

*Primary Examiner* — Gigi Huang
(74) *Attorney, Agent, or Firm* — Louis V. Wollenberger; Joel B. German; Debra D. Condino

(57) ABSTRACT

The present invention provides compositions and uses of an ascomycin macrolactam for the treatment of an unwanted ocular condition occurring in a patient undergoing treatment with a therapeutically active agent for the treatment of cancer.

6 Claims, No Drawings

TREATING UNWANTED OCULAR CONDITIONS USING AN ASCOMYCIN MACROLACTAM

CROSS REFERENCE TO RELATED APPLICATIONS

This application claims the benefit of U.S. Provisional Application No. 60/887,177, filed on Jan. 30, 2007.

Patients undergoing treatment with certain therapeutically active agents can have unwanted ocular conditions occurring as a result of that treatment. In particular, patients undergoing chemotherapy with a therapeutically active agent effective for treatment of a cancer often have unwanted ocular conditions occurring as a result of that treatment. Thus, there is a need to develop methods of treating this unwanted ocular condition in order to improve patient comfort and health.

An aspect of the present invention provides a pharmaceutical composition comprises an ascomycin macrolactam and a therapeutically active agent effective for treatment of a cancer.

Another aspect of the present invention provides the use of an ascomycin macrolactam for the treatment of an unwanted ocular condition occurring in a patient undergoing treatment with a therapeutically active agent for the treatment of cancer. Accordingly, a particular patient group which may benefit from an aspect of the present invention is that of persons having an unwanted ocular condition resulting from the use of a chemotherapy agent.

Another aspect of the present invention provides the use of an ascomycin macrolactam for the treatment of an unwanted ocular condition occurring in a person who is undergoing treatment with an antiviral agent. Accordingly, a particular patient group which may benefit from an aspect of the present invention is that of persons having an unwanted ocular condition resulting from the use of an antiviral agent.

Another aspect of the present invention provides the use of an ascomycin macrolactam for the treatment of an unwanted ocular condition occurring in a person who is undergoing treatment with an immunomodulator. Accordingly, a particular patient group which may benefit from an aspect of the present invention is that of persons having an unwanted ocular conditions resulting from the use of an immunomodulator.

Another aspect of the present invention provides a kit comprising an ascomycin macrolactam and a therapeutically active agent effective for treatment of a cancer. For example, an ascomycin macrolactam and a therapeutically active agent effective for treatment of a cancer may each be packaged in conventional pharmaceutical packaging such as boxes, jars, blister packs, vials, bottles, syringes etc., and the individually packaged components may then be combined to form a kit e.g. by the use of further packaging such as a box, or by joining up the individual packages. When in kit form, the agents can be taken independently of one another, thus allowing the user freedom to decide the temporal relationship between the use of an ascomycin macrolactam and the use of a therapeutically active agent effective for treatment of a cancer.

Aspects of the present invention provide, in part, an ascomycin macrolactam. Ascomycin macrolactams belong to a new group of immunosuppressive, immunomodulatory and anti-inflammatory agents and include, e.g., ascomycin (FK520), tacrolimus (FK506) and pimecrolimus (ASM 981). The main biological effect of ascomycin macrolactams appears to be the inhibition of the synthesis of both Th1 and Th2-type cytokines in target cells.

As used herein, the term "ascomycin macrolactam" means ascomycin, a derivative of ascomycin, such as, e.g., tacrolimus and pimecrolimus, or a prodrug or metabolite of ascomycin or a derivative thereof.

Ascomycin, also called immunomycin, is a structurally complex macrolide produced by *Streptomyces hygroscopicus*. Ascomycin acts by binding to immunophilins, especially macrophilin-12. It appears that ascomycin inhibits the production of Th1 (interferon- and IL-2) and Th2 (IL-4 and IL-10) cytokines. Additionally, ascomycin preferentially inhibits the activation of mast cells, an important cellular component of the atopic response. Ascomycin produces a more selective immunomodulatory effect in that it inhibits the elicitation phase of allergic contact dermatitis but does not impair the primary immune response when administered systemically. The chemical structure of ascomycin is depicted below.

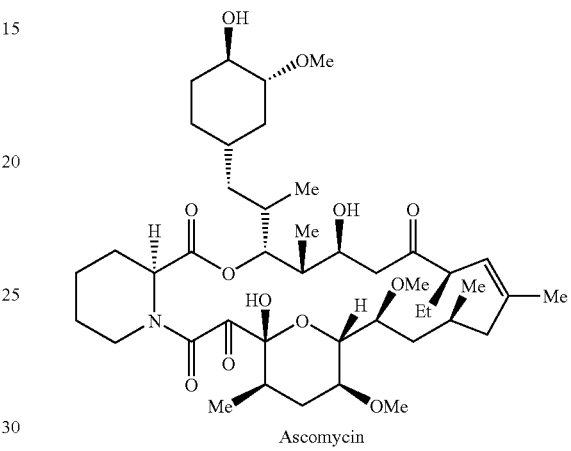

Ascomycin

Tacrolimus (FK506) is a synthetic derivatives of ascomycin. As a calcineurin inhibitor, it works through the FK-binding protein and inhibits the dephosphorylation of nuclear factor of activated T cells (NFAT), thereby preventing the transport of the cytoplasmic component of NFAT to the cell nucleus. This leads to transcriptional inhibition of proinflammatory cytokine genes such as, e.g., interleukin 2, which are dependent on the nuclear factor of activated NFAT. The chemical structure of tacrolimus is depicted below.

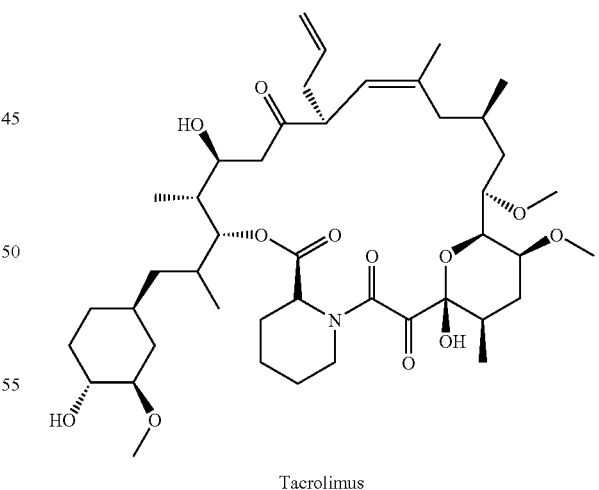

Tacrolimus

Pimecrolimus, an ascomycin derivative, is a calcineurin inhibitor that binds with high affinity to the cytosolic receptor macrophilin-12, inhibiting the calcium-dependent phosphatase calcineurin, an enzyme required for the dephosphorylation of the cytosolic form of the nuclear factor of the activated T cell (NF-AT). It thus targets T cell activation and proliferation by blocking the release of both TH1 and TH2 cytokines such as IF-g, IL-2, -4, -5, and -10.3 It also prevents the production of TNF-a and the release of proinflammatory mediators such as histamine, hexosaminidase, and tryptase from activated mast cells.3 It does not have general antiproliferative activity on keratinocytes, endothelial cells, and fibroblasts, and in contrast to corticosteroids, it does not affect the differentiation, maturation, functions, and viability of human dendritic cells. The chemical structure of pimecrolimus is depicted below.

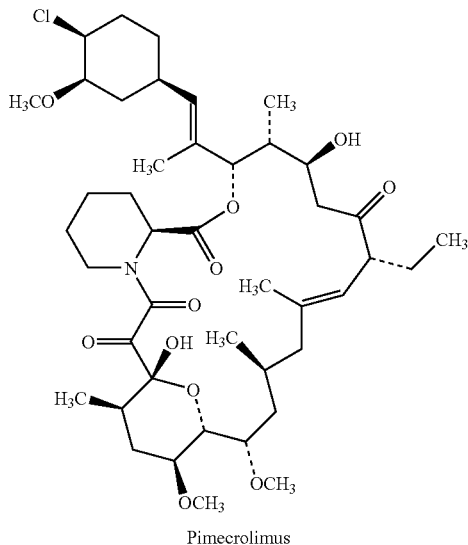 [SMILES: CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@H](Cl)[C@H](OC)C3)[C@H](C)[C@@H](O)CC1=O)[C@H](C)C[C@@H]2OC]

Pimecrolimus

Thus, in an embodiment, an ascomycin macrolactam is used to treat an unwanted ocular condition occurring in a patient undergoing treatment with a therapeutically active agent for the treatment of cancer. In still another embodiment, an ascomycin macrolactam is used to treat an unwanted ocular condition occurring in a person who is undergoing treatment with an antiviral agent. In yet another embodiment, an ascomycin macrolactam is used to treat an unwanted ocular condition occurring in a person who is undergoing treatment with an immunomodulator.

In an aspect of this embodiment, an ascomycin macrolactam can be ascomycin. In aspects of this embodiment, an ascomycin macrolactam can be an ascomycin derivative. In other aspects of this embodiment, there is a difference of less than 5 heavy atoms between the derivative and ascomycin, and all the cycles are intact. A heavy atom is an atom which is not hydrogen. In other words, less than 5 heavy atoms are added to the structure to give the derivative. Alternatively, less than 5 heavy atoms are removed from the structure. Alternatively, less than 5 heavy atoms are substituted with a different heavy atom. In another embodiment, the derivative has a difference of less than 2 heavy atoms from ascomycin.

In an aspect of this embodiment, an ascomycin macrolactam can be tacrolimus. In aspects of this embodiment, an ascomycin macrolactam can be a tacrolimus derivative. In other aspects of this embodiment, there is a difference of less than 5 heavy atoms between the derivative and tacrolimus, and all the cycles are intact. A heavy atom is an atom which is not hydrogen. In other words, less than 5 heavy atoms are added to the structure to give the derivative. Alternatively, less than 5 heavy atoms are removed from the structure. Alternatively, less than 5 heavy atoms are substituted with a different heavy atom. In another embodiment, the derivative has a difference of less than 2 heavy atoms from tacrolimus.

In an aspect of this embodiment, an ascomycin macrolactam can be pimecrolimus. In aspects of this embodiment, a tacrolimus macrolactam can be a pimecrolimus derivative. In other aspects of this embodiment, there is a difference of less than 5 heavy atoms between the derivative and pimecrolimus, and all the cycles are intact. A heavy atom is an atom which is not hydrogen. In other words, less than 5 heavy atoms are added to the structure to give the derivative. Alternatively, less than 5 heavy atoms are removed from the structure. Alternatively, less than 5 heavy atoms are substituted with a different heavy atom. In another embodiment, the derivative has a difference of less than 2 heavy atoms from pimecrolimus.

Aspects of the present invention provide, in part, an unwanted ocular condition. An ocular condition includes, without limitation, nasolacrimal stenosis, canalicular stenosis, lacrimal duct stenosis, punctal stenosis, chemotherapy induced ocular toxicity, lacrimation, abnormal lacrimation, epiphora (excessive tearing), nasolacrimal blockage, dacryocystitis, keratitis, keratoconjunctivitis, conjunctivitis, or a combination thereof.

While not intending to limit the scope of the invention in any way, the following therapeutically active agents may cause lacrimal duct stenosis: docetaxel.

While not intending to limit the scope of the invention in any way, the following therapeutically active agents may cause punctal stenosis: docetaxel.

While not intending to limit the scope of the invention in any way, the following therapeutically active agents may cause lacrimation: interferon alfa-2b, recombinant, doxorubicin hydrochloride, irinotecan hydrochloride, fluorouracil, docetaxel, and zalcitabine.

While not intending to limit the scope of the invention in any way, the following therapeutically active agents may cause abnormal lacrimation: mycophenolate motefil, mycophenolate motefil hydrochloride, imatinib mesylate, ritumixab, and rimantadine hydrochloride.

While not intending to limit the scope of the invention in any way, the following therapeutically active agents may cause keratitis: Amantadine Hydrochloride, Erlotinib, Bexarotene, and Voriconazole.

While not intending to limit the scope of the invention in any way, the following therapeutically active agents may cause keratoconjunctivitis: Capecitabine.

While not intending to limit the scope of the invention in any way, the following therapeutically active agents may cause conjunctivitis: Risedronate Sodium, Leflunomide, Mycophenolate Mofetil, Oxaliplatin, Cetuximab, Ribavirin, Rituximab, Basiliximab, Erlotinib, Capecitabine, Doxorubicin Hydrochloride, Imiquimod, Amphotericin B, liposomal, Zolpidem Tartrate, Glatiramer Acetate, Epirubicin Hydrochloride, Saquinavir, Enfuvirtide, Imatinib Mesylate, Gefitinib, Lamotrigine, Delavirdine Mesylate, Rituximab, Ivermectin, Palivizumab, Oseltamivir Phosphate, Bexarotene, Docetaxel, Abacavir Sulfate, Lamivudine, Zidovudine, Voriconazole, Nevirapine, Ribavirin, and Abacavir Sulfate.

Additionally, one or more of the ocular conditions disclosed herein may be associated with the following therapeutically active agents: abacavir sulfate, amantadine hydrochloride, amphotericin B, basiliximab, bexarotene, capecitabine, cetuximab, delavirdine mesylate, docetaxel, doxorubicin hydrochloride, enfuvirtide, epirubicin hydrochloride, erlotinib, fluorouracil, gefitinib, glatiramer acetate, imatinib mesylate, imiquimod, interferon alfa-2b, irinotecan hydrochloride, ivermectin, lamivudine, lamotrigine, leflunomide, mycophenolate mofetil, mycophenolate mofetil hydrochloride, nevirapine, oseltamivir phosphate, palivizumab, ribavirin, rimantadine hydrochloride, risedronate sodium, rituximab, saquinavir, voriconazole, zalcitabine, zidovudine, and zolpidem tartrate.

Aspects of the present invention provide, in part, a therapeutically active agent for the treatment of cancer. A therapeutically active agent for the treatment of cancer includes a chemotherapy agent, and antiviral agent and an immunomodulator.

Aspects of the present invention provide, in part, a chemotherapy agent. An ascomycin macrolactam may be used with any chemotherapy agent associated with the appearance of an unwanted ocular condition, including, without limitation, Paclitaxel and derivatives thereof, such as, e.g., Docetaxel; Doxorubicin Hydrochloride; Irinotecan Hydrochloride; Fluorouracil; Imatinib Mesylate; and Rituximab.

Derivatives of Paclitaxel generally include the macrocycle shown below, where derivatives are formed at a hydroxyl moiety.

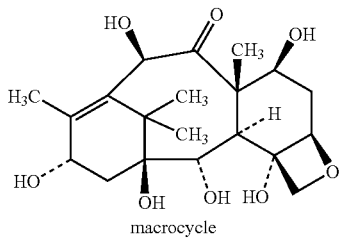

macrocycle

Chemotherapeutic agents incorporating this structure are thus contemplated. For example, the structures of Paclitaxel and Docetaxel are shown below.

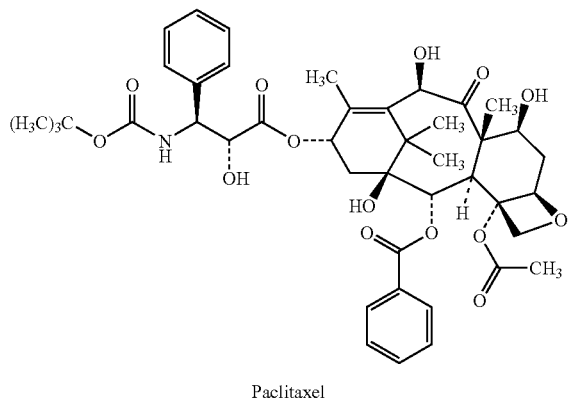 [SMILES: CC(=O)O[C@@]12CO[C@@H]1C[C@H](O)[C@@]1(C)C(=O)[C@H](O)C3=C(C)[C@@H](OC(=O)[C@H](O)[C@@H](NC(=O)OC(C)(C)C)c4ccccc4)C[C@@](O)([C@@H](OC(=O)c4ccccc4)[C@H]21)C3(C)C]

Paclitaxel

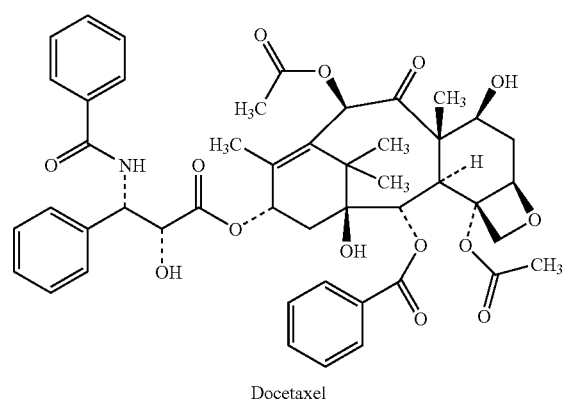

Docetaxel

Thus, in an embodiment, an ascomycin macrolactam is used to treat an unwanted ocular condition occurring in a patient undergoing treatment with a therapeutically active agent for the treatment of cancer. In an embodiment, the therapeutically active agent for the treatment of cancer can be a chemotherapy agent. In an aspect of this embodiment, a chemotherapy agent can be Paclitaxel. In another aspect of this embodiment, a chemotherapy agent can be a Paclitaxel derivative. In yet other aspects of this embodiment, a chemotherapy agent can be, e.g., Docetaxel, Doxorubicin Hydrochloride, Irinotecan Hydrochloride, Fluorouracil, Imatinib Mesylate, or Rituximab. In still other aspects of this embodiment, a chemotherapy agent can be, e.g., Paclitaxel, a Paclitaxel derivative, Docetaxel, Doxorubicin Hydrochloride, Irinotecan Hydrochloride, Fluorouracil, Imatinib Mesylate, Rituximab, or any combination thereof.

Aspects of the present invention provide, in part, an antiviral agent. An ascomycin macrolactam may be used with any antiviral agent associated with the appearance of an unwanted ocular condition, including, without limitation, Zalcitabine, and Rimantadine Hydrochloride.

Thus, in an embodiment, an ascomycin macrolactam is used to treat an unwanted ocular condition occurring in a patient undergoing treatment with an antiviral agent. In an embodiment, an antiviral agent can be Zalcitabine, Rimantadine Hydrochloride, or any combination thereof.

Aspects of the present invention provide, in part, an immunomodulator. An ascomycin macrolactam may be used with any immunomodulator associated with the appearance of an unwanted ocular condition, including, without limitation, Interferon alfa-2b, Recombinant Mycophenolate Mofetil, and Mycophenolate Mofetil Hydrochloride.

Thus, in an embodiment, an ascomycin macrolactam is used to treat an unwanted ocular condition occurring in a patient undergoing treatment with an immunomodulator. In an embodiment, an immunomodulator can be Interferon alfa-2b, Recombinant Mycophenolate Mofetil, Mycophenolate Mofetil Hydrochloride, or any combination thereof.

One embodiment is a method comprising administering an ascomycin macrolactam to an eye of a mammal in combination with administration of a therapeutically active agent to said mammal, said therapeutically active agent being an chemotherapy agent or an antiviral agent, wherein said method is effective in preventing or treating an ocular condition associated with the use of said therapeutically active agent.

Aspects of the present invention provide, in part, an administration of an ascomycin macrolactam. As used herein, the term "administration" means any delivery mechanism that provides an ascomycin macrolactam to a patient that potentially results in a clinically, therapeutically, cosmetically or experimentally beneficial result. An ascomycin macrolactam useful in the methods disclosed in the present specification can be administered to an individual by any of a variety of routes depending, for example, on the type and location of the unwanted ocular condition to be treated, the ascomycin macrolactam, or other compound to be included in the composition, and the history, risk factors and symptoms of the patient. Routes of administration suitable for the methods of the invention include both local and systemic administration. Local administration results in significantly more ascomycin macrolactam being delivered to a specific location as compared to the entire body of the subject, whereas, systemic administration results in delivery of an ascomycin macrolactam to essentially the entire body of the subject. An ascomycin macrolactam can also be administered peripherally. As used herein, the term "peripheral administration" or "administered peripherally" means introducing an ascomycin macrolactam into an individual outside of the central nervous system. Peripheral administration encompasses any route of administration other than direct administration to the spine or brain. As such, it is clear that intrathecal and epidural administration as well as cranial injection or implantation is not within the scope of the term "peripheral administration" or "administered peripherally." Thus, administration of the therapeutically active agent is not limited to the eye, but may include systemic administration via oral, intravenous, rectal, or other means; or administration locally to any part of the body by injection, implantation, topical administration, or other means.

Administration of an ascomycin macrolactam can be by a variety of routes including, without limitation, orally in any acceptable form, such as, e.g., tablet, liquid, capsule, powder, or the like; topically in any acceptable form, such as, e.g., patch, drops, creams, gels or ointments; by injection, in any acceptable form, such as, e.g., intravenous, intraperitoneal, intramuscular, subcutaneous, parenteral or epidural; and by implant, such as, e.g., subcutaneous pump, intrathecal pump, suppository, bioerodible delivery system, non-bioerodible delivery system or other implanted extended or slow release device or formulation. An exemplary list of biodegradable polymers and methods of use are described in, e.g., Handbook of Biodegradable Polymers (Abraham J. Domb et al., eds., Overseas Publishers Association, 1997); Controlled Drug Delivery: Designing Technologies for the Future (Kinam Park & Randy J. Mrsny eds., American Chemical Association, 2000); Vernon G. Wong, Method for Reducing or Preventing Transplant Rejection in the Eye and Intraocular Implants for Use Therefor, U.S. Pat. No. 6,699,493 (Mar. 2, 2004); Vernon G. Wong & Mae W. L. Hu, Methods for Treating Inflammation-mediated Conditions of the Eye, U.S. Pat. No. 6,726,918 (Apr. 27, 2004); David A. Weber et al., Methods and Apparatus for Delivery of Ocular Implants, U.S. Patent Publication No. US2004/0054374 (Mar. 18, 2004); Thierry Nivaggioli et al., Biodegradable Ocular Implant, U.S. Patent Publication No. US2004/0137059 (Jul. 15, 2004).

Administration of an ascomycin macrolactam need not exactly overlap in time with the administration of a therapeutically active agent for the treatment of cancer, an antiviral agent or an immunomodulator. For example, an ascomycin macrolactam might be administered to a mammal before the patient receives any of the therapeutically active agent to avoid the onset of the ocular condition. In another example, an ascomycin macrolactam might be administered after the patient has begun to receive a therapeutically active agent for the treatment of cancer, an antiviral agent or an immunomodulator. In another example, an ascomycin macrolactam might be administered after the patient has ceased receiving a therapeutically active agent for the treatment of cancer, an antiviral agent or an immunomodulator. Administration of an ascomycin macrolactam to a patient might also be simultaneous with the administration of a therapeutically active agent for the treatment of cancer, an antiviral agent or an immunomodulator. Thus, any time relationship may exist between the patient receiving an ascomycin macrolactam and a therapeutically active agent for the treatment of cancer, an antiviral agent or an immunomodulator, provided that the use of the former is reasonably related to treatment or prophylaxis of a condition associated with the later. A therapeutically active agent for the treatment of cancer, an antiviral agent or an immunomodulator is administered in the usual manner known in the art for the condition being treated.

Alternatively, a therapeutically active agent and an ascomysin macrolactam may be administered with a therapeutically active agent for the treatment of cancer, an antiviral agent or an immunomodulator as a single pharmaceutical composition. Useful compositions are disclosed in the following patent applications, each of which is expressly incorporated by reference herein: U.S. patent application Ser. No. 11/181,409, filed on Jul. 13, 2005; U.S. patent application Ser. No. 11/181,509, filed on Jul. 13, 2005; U.S. patent application Ser. No. 11/181,187, filed on Jul. 13, 2005; U.S. patent application Ser. No. 11/181,178, filed on Jul. 13, 2005; U.S. patent application Ser. No. 11/181,428, filed on Jul. 13, 2005, now U.S. Pat. No. 7,202,209; U.S. patent application Ser. No. 11/255,821, filed on Oct. 19, 2005, now U.S. Pat. No. 7,288,520; U.S. patent application Ser. No. 11/161,218, filed on Jul. 27, 2005; and U.S. Provisional Patent Application Ser. No. 60/727,684, filed on Oct. 17, 2005, now abandoned.

An ascomysin macrolactam useful in a method disclosed in the present specification is administered to a patient in an effective amount. As used herein, the term "effective amount" when used in reference to treating an unwanted ocular condition means the minimum dose necessary to achieve the desired therapeutic effect and includes a dose sufficient to reduce a symptom associated with an unwanted ocular condition. In aspects of this embodiment, an effect amount of an ascomysin macrolactam reduces a symptom associated with an unwanted ocular condition by, e.g., at least 30%, at least 40%, at least 50%, at least 60%, at least 70%, at least 80%, at least 90% or at least 100%. In other aspects of this embodiment, an effect amount of an ascomysin macrolactam reduces a symptom associated with an unwanted ocular condition by, e.g., at most 30%, at most 40%, at most 50%, at most 60%, at most 70%, at most 80%, at most 90% or at most 100%.

The appropriate effective amount to be administered for a particular application of the methods can be determined by those skilled in the art, using the guidance provided herein. For example, an effective amount can be extrapolated from in vitro assays and in vivo administration studies using animal models prior to administration to humans. Such a effect amount generally is in the range of 0.1-1000 mg/day and can be, e.g., in the range of 0.1-500 mg/day, 0.5-500 mg/day, 0.5-100 mg/day, 0.5-50 mg/day, 0.5-20 mg/day, 0.5-10 mg/day or 0.5-5 mg/day. Additionally, such an effective amount can be a medicament comprising about 0.01% to about 2.0% of an ascomysin macrolactam, about 0.1% to about 1.0% of an ascomysin macrolactam, about 0.5% to about 1.5% of an ascomysin macrolactam, about 0.05% to about 0.15% of an ascomysin macrolactam, about 0.01% to about 0.15% of an ascomysin macrolactam, about 0.005% to about 0.2% of an ascomysin macrolactam, about 0.01% to about 0.03% of an ascomysin macrolactam, or about 0.03% to about 0.05% of an ascomysin macrolactam.

An effective dose of an ascomysin macrolactam useful for reducing a symptom of an unwanted ocular condition in a patient will depend upon the particular ascomysin macrolactam used, the particular unwanted ocular condition being treated, and the route administration. In addition, the actual amount of the effective dose of an ascomysin macrolactam to be administered to a patient will be determined by a physician taking into account the cause of the particular unwanted ocular condition, the severity of the particular unwanted ocular condition and the particular characteristics of the patient, such as age, weight, general health and the like. Where repeated administration is used, the frequency of administration depends, in part, on the half-life of the ascomysin macrolactam. One skilled in the art will recognize that the condition of the patient can be monitored throughout the course of therapy and that the effective amount of an ascomysin macrolactam that is administered can be adjusted accordingly. It is also understood that the frequency and duration of dosing will be dependent, in part, on the relief desired and the half-life of the ascomysin macrolactam.

Although there has been hereinabove described pharmaceutical compositions for the purpose of illustrating the manner in which the invention may be used to advantage, it should be appreciated that the invention is not limited thereto.

Accordingly, any and all modifications, variations, or equivalent arrangements, which may occur to a person of ordinary skill in the art, should be considered to be within the scope of the present invention as defined in the appended claims.

EXAMPLES

Example 1

Treatment of an Ocular Condition with an Ascomycin Macrolactam Resulting from a Chemotherapy Agent A 54 year old woman undergoing docetaxel treatments every three weeks as part of her breast cancer therapy developed epiphora during the seventh week. Physician examination reveals the cause of the excessive tearing to be punctal stenosis. The patient receives a medication containing 0.1% tacrolimus. After one week of daily treatment the excessive tearing subsides.

Example 2

Preventative Treatment of an Ocular Condition with an Ascomycin Macrolactam Prior to a Chemotherapy Agent A 63 year old woman is diagnosed with metastatic breast cancer. Her physician decides that the best course of cancer therapy includes weekly docetaxel treatments. In order to reduce or prevent the occurrence of unwanted ocular conditions as a result of the docetaxel treatments, the physician also prescribes a medication containing 1.0% pimecrolimus to be administered during the entire course of docetaxel treatments. The patient does not exhibit epiphora or show any symptoms of an ocular condition, such as, e.g., nasolacrimal stenosis, canalicular stenosis, lacrimal duct stenosis, or punctal stenosis.

Example 3

Treatment of an Ocular Condition with an Ascomycin Macrolactam After a Chemotherapy Treatment A physician diagnosis a 67 year old man complaining of excessive tearing with epiphora. The physician determines that the cause of this excessive tearing was canalicular stenosis, and believes that this ocular condition was brought on by the man's prostate cancer therapy, which included docetaxel treatments every three weeks. The patient receives a medication containing 0.03% acromycin. After one week of daily treatment the excessive tearing subsides.

What is claimed:

1. A method for treating punctal stenosis occurring in a patient undergoing cancer treatment with docetaxel, the method comprising the step of administering a therapeutically effective amount of an ascomycin macrolactam to an eye of the patient, wherein the ascomycin macrolactam is ascomycin or pimecrolimus.

2. The method of claim 1, wherein the ascomycin macrolactam is administered before administration of the docetaxel.

3. The method of claim 1, wherein the ascomycin macrolactam is administered after administration of the docetaxel.

4. The method of claim 1, wherein the ascomycin macrolactam is administered simultaneously with administration of the docetaxel.

5. The method of claim 1, wherein the ascomycin macrolactam is ascomycin.

6. The method of claim 1, wherein the ascomycin macrolactam is pimecrolimus.

* * * * *